United States Patent [19]

Benajam et al.

[11] Patent Number: 4,587,103

[45] Date of Patent: May 6, 1986

[54] DEVICE FOR ACTUATING AN AUTOMATIC DEVICE COMPRISING A PLURALITY OF COMBINED MOBILE MEMBERS

[75] Inventors: Alain C. A. Benajam, Bobigny; Jean-Michel Lachenal, Fresnes, both of France

[73] Assignee: Le Materiel Biomedical, Paris, France

[21] Appl. No.: 657,530

[22] Filed: Oct. 4, 1984

[51] Int. Cl.[4] ............................................. G01N 33/00
[52] U.S. Cl. ........................................ 422/67; 422/73; 92/12.1; 60/581; 60/591
[58] Field of Search ........................... 422/64, 67, 73; 92/12.1; 60/581, 591

[56] References Cited

U.S. PATENT DOCUMENTS

| | | | |
|---|---|---|---|
| 3,767,364 | 10/1973 | Ritchie et al. | 422/64 X |
| 3,883,308 | 5/1975 | Matte | 422/64 |
| 4,439,986 | 4/1984 | Snitgen | 60/591 X |
| 4,486,097 | 12/1984 | Riley | 422/64 X |

Primary Examiner—Arthur Kellogg
Attorney, Agent, or Firm—Fisher, Christen & Sabol

[57] ABSTRACT

The present invention relates to a device for actuating an automatic device comprising a plurality of combined mobile members, wherein this device comprises an electric motor actuating a hydraulic master jack which in turn actuates a plurality of hydraulic slave jacks connected to said mobile members.

5 Claims, 9 Drawing Figures

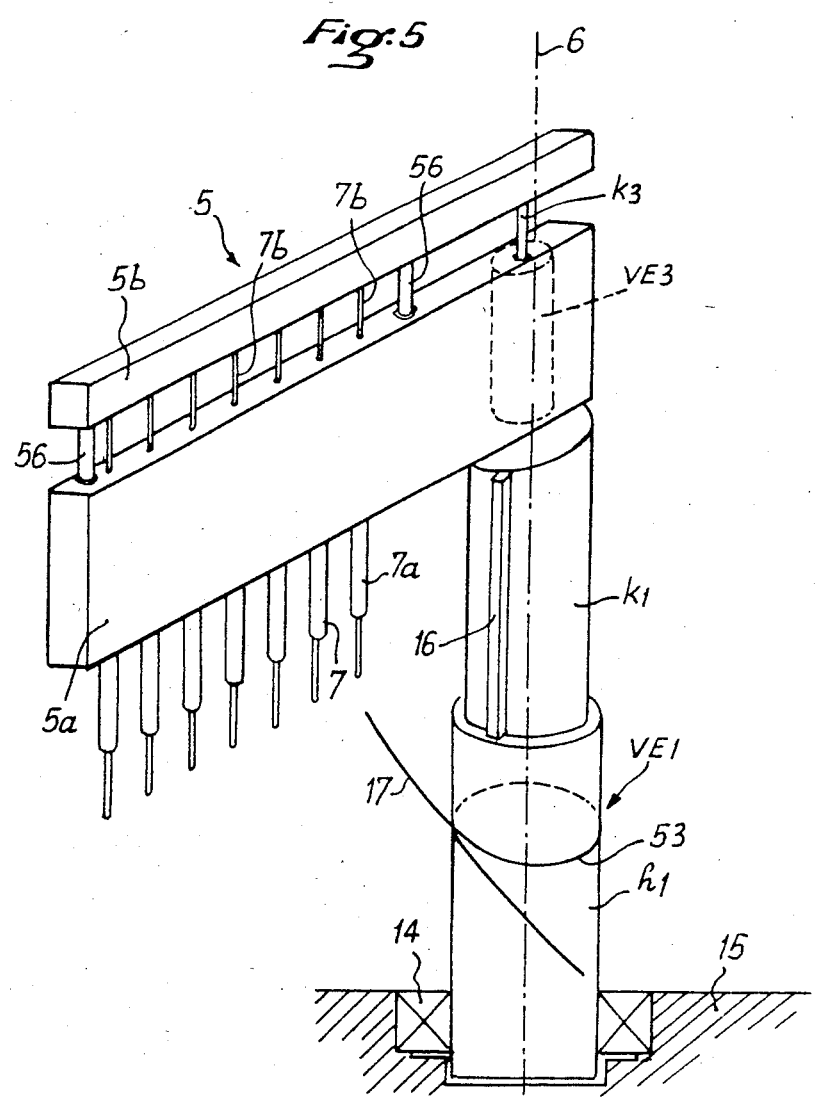
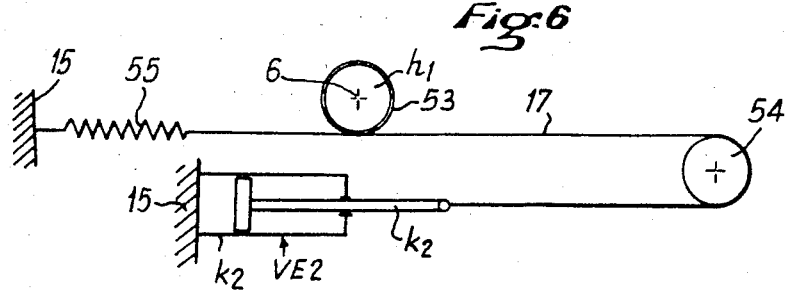

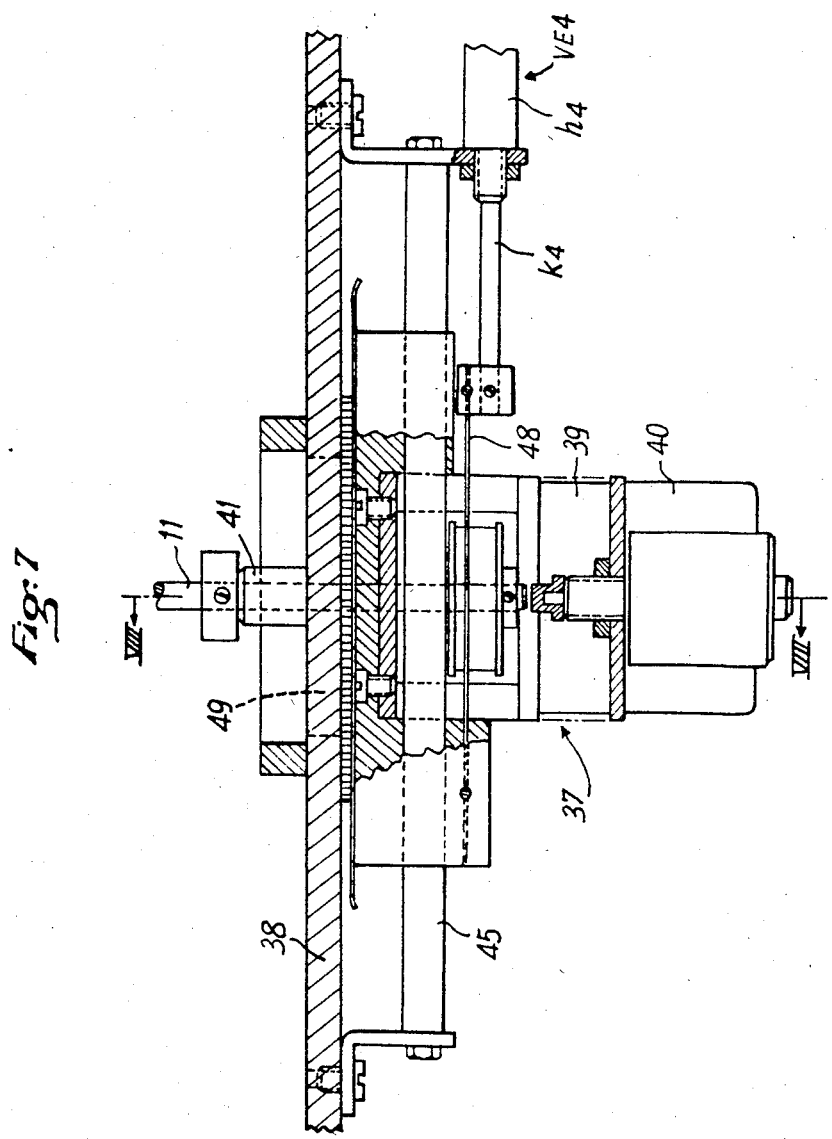

DEVICE FOR ACTUATING AN AUTOMATIC DEVICE COMPRISING A PLURALITY OF COMBINED MOBILE MEMBERS

The present invention relates to a device for actuating an automatic device comprising a plurality of combined mobile members, i.e. mounted to move with respect to one another.

To drive the mobile members of such an automatic device, electric motors, for example stepping motors, are generally used.

These electric motors are "embarked", i.e. borne respectively by that of said mobile members with respect to which the mobile member which they actuate is mounted.

As they are borne by mobile members of the automatic device, these motors must be chosen to be as small as possible, in order not to encumber the rapidity of operation of said device, nor render prohibitive the power necessary for this operation. However, even of small size, such electric motors are still heavy and, moreover, they are not very reliable and their power is weak. The automatic devices of this type therefore present limited operational speed, reliability and power, whilst consuming a relatively large amount of energy.

It is an object of the present invention to overcome these drawbacks and to provide an actuating device rendering the automatic device rapid, precise, reliable and powerful without consuming a great deal of energy.

To this end, according to the invention, the device for actuating an automatic device comprising a plurality of combined mobile members is noteworthy in that it comprises a single electric motor, for example of the stepping type, capable of rotating in both directions of rotation, means for converting the movement of rotation of said electric motor into a movement of translation, a hydraulic master jack whose piston is controlled in translation by said movement converting means, a plurality of hydraulic ducts connected in parallel to the cylinder of said master jack, a plurality of electro-valves each mounted on one of said hydraulic ducts, a device for controlling said electro-valves and a plurality of hydraulic slave jacks whose cylinders are each connected to one of said hydraulc ducts and whose pistons are each connected to one of said mobile members.

Thus, when the piston of the hydraulic master jack moves under the action of the electric motor and the movement converting means, this results in a corresponding movement of the piston of that or those of the slave jacks (and therefore of the mobile member connected thereto) or which the associated electro-valve is opened by said control device.

It will be noted that, in the actuating device according to the invention, the electric motor, the movement converting means, the hydraulic master jack, the electro-valves and the control device may be mounted in fixed manner and that possibly only the slave jacks must be mounted on one of the mobile parts of the automatic device. In that case, they are connected to the electro-valves by portions of supple ducts. It is then possible to choose an electric motor of large dimensions, therefore reliable, powerful and with high-performance.

In known manner, the movement converting means may be of the screw and nut type. In that case, in order to be sure that, in both directions of translation of the pistons of the master and slave jacks, the same faces of the thread of the screw and of the thread of the nut abut against each other, so as to annul the screw-nut clearance and therefore to count the same number of steps of the motor in both directions of rotation thereof for a to and fro movement of the piston of the master jack, a source of pressurized fluid is provided, connected via a plurality of lines to the cylinders of the slave jacks, on the piston side thereof opposite the connecting ducts of the master jack. In this way, the pressure exerted by this source of fluid on the piston of the slave jacks and therefore on the piston of the master jack (via the hydraulic fluid) makes it possible, upon return, to pre-stress said nut, in the direction of the motor.

It will be noted that, in the device according to the invention, the different mobile members automatically return to a determined rest position at the end of cycle, corresponding to the end-of-stroke position of the pistons of the slave jacks repelled by the pressurized fluid from said source.

The device according to the invention has numerous applications. However, it is particularly appropriate for use in a device for detecting and quantifying agglutinates capable of being formed, under the action of at least one reagent, by particles in suspension in a liquid, for example of the type used in immunohaematology, particularly with a view to determining blood groups.

Such a known device for detecting and quantifying agglutinates uses recipients of which at least the bottoms are transparent, and may employ, for detecting and quantifying agglutinates likely to be formed under the action of at least one liquid reagent, by particles in suspension in doses of liquids to be tested contained in said recipients, a linear arrangement of a plurality of photosensitive elements observing by transparency the bottoms of said recipients containing the possible agglutinates by scanning said bottoms of said recipients, so as to form n x m points of observation distributed over a rectangular or square surface occupying the major part of the surface of the bottom of each recipient. Such recipients may be constituted by recesses distributed along radii of a horizontal transparent disc adapted to rotate about its vertical axis and an oscillating arm rotating about a vertical axis adapted to be raised and lowered and provided with means for taking and restoring liquid doses may be provided for taking such doses from reservoirs of reagents and liquids to be tested and for conducting them into said recesses in the rotating disc, whilst said linear arrangement of photosensitive elements is disposed in fixed manner at right angles to a diameter of the transparent disc and the axis of rotation of the disc is mounted to move in translation at right angles to said linear arrangement of photosensitive elements.

Thus, via its means for taking and restoring liquid doses, which may be syringes for example, the sliding, oscillating arm may introduce into each recess of the rotating disc a liquid to be tested and the corresponding reagent. After reaction, each recess is examined by the arrangement of photosensitive elements during translation of the axis of the disc, the amplitude of such translation being sufficient for all the recesses of a radius of the disc to be observed, each in m steps.

Furthermore, the linear arrangement of photosensitive elements may be disposed at right angles to the vertical plane passing through the vertical axes of the transparent disc and of the oscillating arm, on the side of the axis of the disc opposite said oscillating arm, with the result that the disc must effect a rotation through 180° for a radius of recesses laden with doses of liquids to be tested and with reagent to be read by said arrangement.

Thus, in such a device according to the invention, four slave jacks are provided, namely a first for the rotation of the oscillating arm, a second for raising and lowering said arm, a third for taking and restoring liquid doses and the fourth for the translation of the axis of rotation of the disc.

The invention will be more readily understood on reading the following description with reference to the accompanying drawings, in which:

FIG. 1 gives the block diagram of the actuating device according to the invention.

Figure 2:
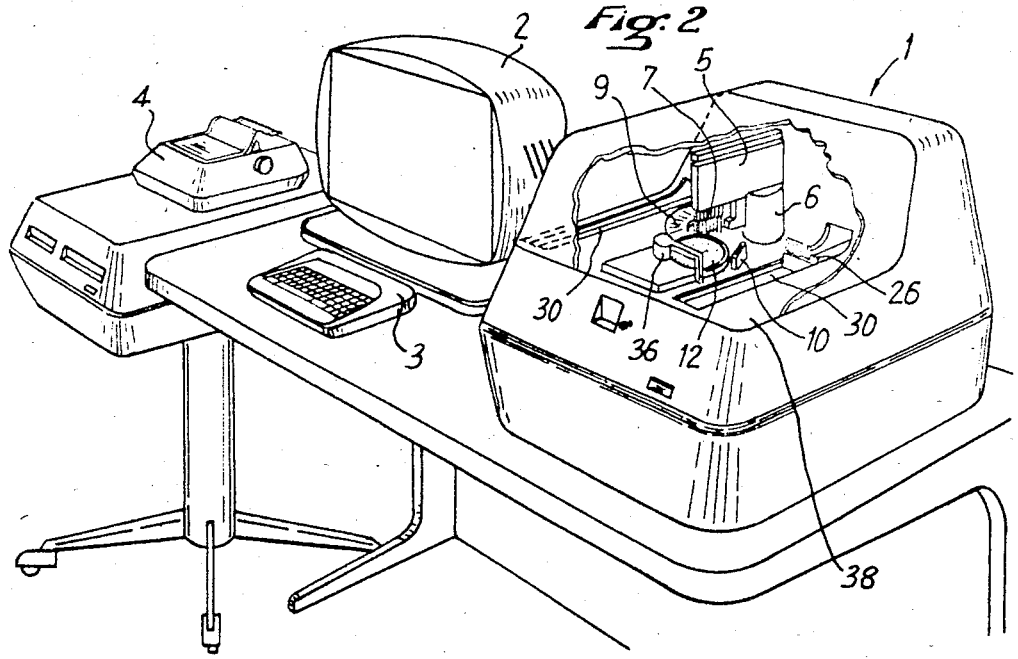
FIG. 2 is an overall view in perspective, with parts torn away, of an automatic installation for determining blood groups, moved by the actuating device according to the invention.
Figure 3:
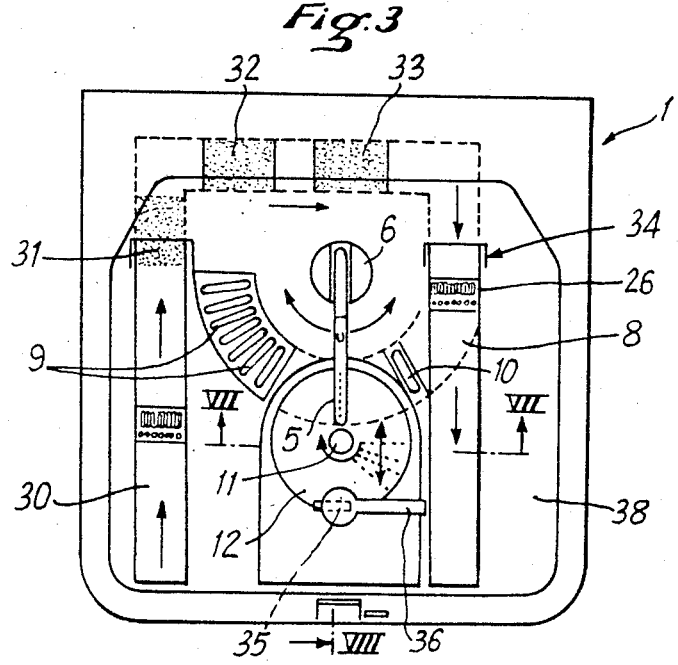
FIG. 3 is a simplified plan view of part of the installation of FIG. 2.

FIG. 5 schematically illustrates in perspective the sliding, oscillating arm of the installation of FIGS. 2 and 3 and the motorization thereof.

FIG. 6 schematically illustrates the rotation of the oscillating arm.

Figure 8:
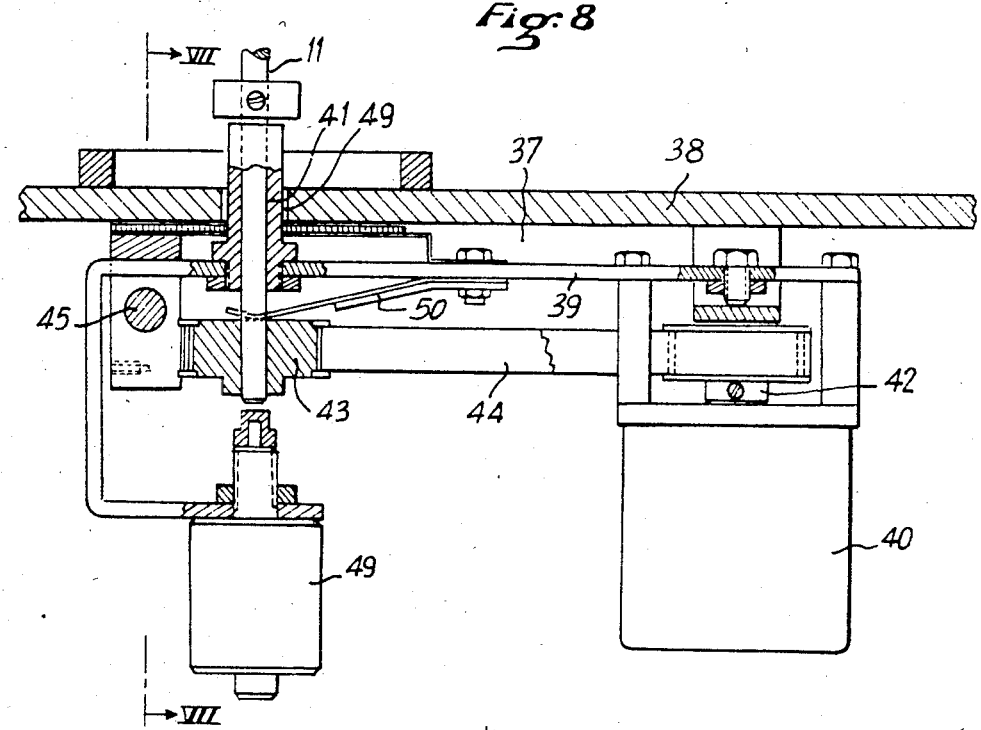

FIGS. 7 and 8 are sections respectively along lines VII—VII and VIII—VIII of FIG. 3.

Figure 9:
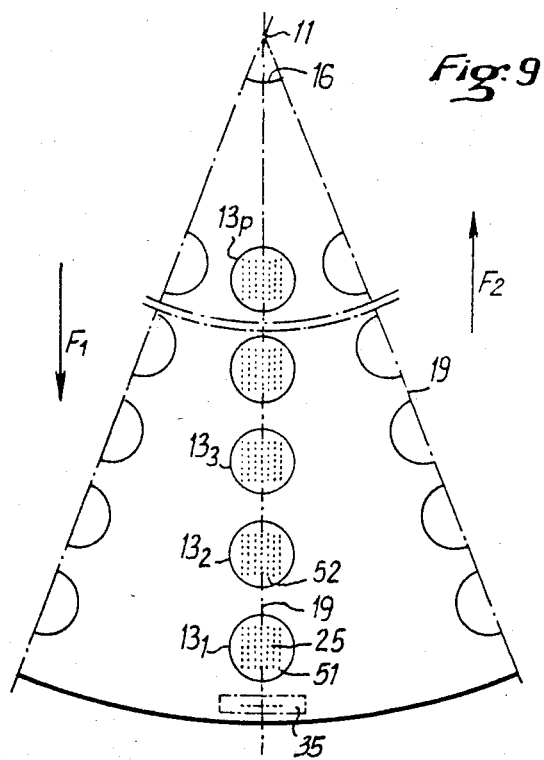

FIG. 9 schematically illustrates the process of reading the agglutinates.

In these Figures, like references designate like elements.

Figure 1:
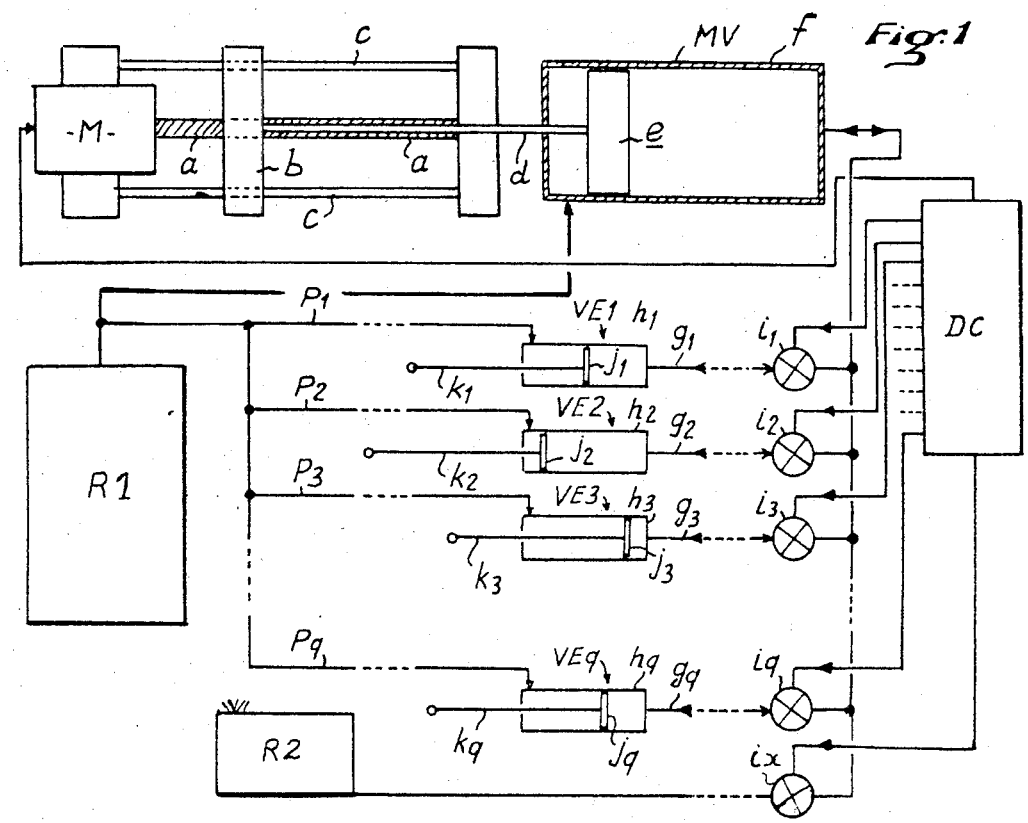

Referring now to the drawings, the actuating device according to the invention shown in FIG. 1 comprises a control device DC and an electric stepping motor M which may rotate in both directions of rotation and of which the driven shaft is constituted by a screw a. A nut b, prevented from rotating by slide guides c, is in mesh with screw a. This nut b is connected by a rod d with the piston e of a master jack MV of which the cylinder f is filled with a hydraulic liquid and is connected, by a plurality of ducts $g_1$, $g_2$, $g_3$, ... $g_q$ in parallel, to the cylinders $h_1$, $h_2$, $h_3$, ... $h_q$ of a plurality of slave jacks $VE_1$, $VE_2$, $VE_3$, ... $VE_q$. On each of ducts $g_1$ to $g_q$ there is mounted a three-way electro-valve $i_1$ to $i_q$, controlled by the electronic control device DC. The latter controls said electro-valves $i_1$ to $i_q$ independently of one another and possible sequentially in a cycle.

The slave jacks $VE_1$ to $VE_q$ are each provided with a piston $j_1$ to $j_q$ connected by a rod $k_1$ to $k_q$ to a mobile member (not shown in FIG. 1) to be moved.

The hydraulic liquid capacity of the cylinder f of the master jack MV is at least equal to the sum of the capacities of cylinders $h_1$ to $h_q$ of the slave jacks $VE_1$ to $VE_q$. Furthermore, the device of FIG. 1 comprises a reservoir R1 of pressurized fluid (gas or liquid) connected by a plurality of ducts $p_1$ to $p_q$ to the cylinders $h_1$ to $h_q$ of the slave jacks $VE_1$ to $VE_q$ respectively, on the side of piston $j_1$ to $j_q$ opposite the ducts $g_1$ to $g_q$. The reservoir R1 is also connected to cylinder f of the master jack MV on the side of piston e opposite the electro-valves $i_1$ to $i_q$. The device of FIG. 1 further comprises a reservoir R2 containing a reserve of hydraulic liquid at atmospheric pressure. Each slave jack $VE_1$ to $VE_q$ and the master jack MV may be connected to the reservoir R2 via the electro-valves $i_1$ to $i_q$ and an electro-valve $i_x$, also controlled by the control device DC.

In this way, when the motor M rotates in the direction for which the nut b moves from left to right in FIG. 1, the piston e of the master jack$^{MV}$ moves like said nut.

Consequently, hydraulic liquid is driven into ducts $g_1$ to $g_q$ and the pistons $j_1$ to $j_q$ of those of the slave jacks $VE_1$ to $VE_q$ of which the corresponding electro-valve $i_1$ to $i_q$ is opened by the control device DC, are displaced towards the left in the Figure against the action of the pressure of the fluid of reservoir R1. The mobile members connected to the corresponding piston rods $k_1$ to $k_q$ are therefore displaced in a first direction.

On the other hand, when the motor M rotates in the direction for which the nut b moves from right to left in FIG. 1, the pistons $j_1$ to $j_q$ of those of the slave jacks $VE_1$ to $VE_q$ whose electro-valve $i_1$ to $i_q$ is opened by the device DC, are displaced towards the right in the Figure under the combined action of the suction of the piston e of the master jack MV and of the thrust of the pressurized fluid or source R1. The mobile members connected to the corresponding piston rods $k_1$ to $k_q$ are therefore displaced in the direction opposite the first.

Moreover, the electro-valves $i_1$ to $i_q$ and $i_x$ make it possible to place jacks MV and $VE_1$ to $VE_q$ in communication with the source R2 of which the fluid is at atmospheric pressure. In this way:

- it is possible to fill each jack independently upon an initial venting operation of the hydraulic circuit;
- it is possible mechanically to initialize all the jacks at the end of each cycle;
- such initialization overcomes the variations in density of the hydraulic fluid and therefore the variations of displacement, during change of temperature.

Of course, the control device DC coordinates in time, in accordance with the cycle to be effected, the control of the electro-valves $i_x$ and $i_1$ to $i_q$, as well as the rotation of motor M.

The installation for determining blood groups, shown in FIG. 2, comprises a device 1 for detecting and quantifying agglutinates, associated with a display device 2, a control device 3 and a printout device 4. The whole installation is controlled by a microprocessor (not shown) in accordance with a process not described hereinafter. Part of this microprocessor constitutes the control device DC of FIG. 1.

As also shown in FIG. 3, the device 1 comprises a horizontal oscillating arm 5 adapted to rotate about a vertical axis 6, and to rise and lower vertically. The arm 5 carries a plurality of vertical syringes 7 whose pistons may be actuated to suck up or deliver a liquid. When the arm 5 oscillates about vertical axis 6, the syringes 7 sweep over an annular zone 8.

In this annular zone 8 there are provided recipients 9 containing reagents, from each of which the vertical syringes 7 may take a reagent, and a rinsing recipient 10.

Furthermore, the device 1 comprises a vertical pin 11 adapted to rotate a disc 12 made of transparent material in which recesses 13 are made.

The recesses 13 of disc 12 are distributed at a plurality of points 18 lying at the intersection of radii 19 and of concentric circles 20.

Figure 4:
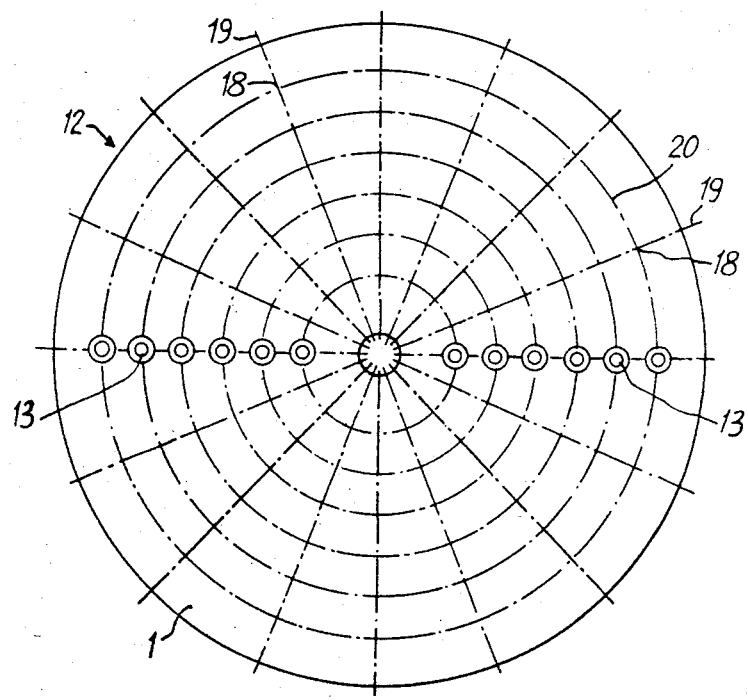
FIG. 4 is a plan view of a disc with recesses used in the device according to the invention.

Only a few recesses 13 have been shown in FIG. 4 in order to render the drawing clearer.

The annular zone 8 swept over by syringes 7 intersects the disc 12 so that it is possible to fill all the recesses 13 lying on a radius 19 of the disc 12 with doses of reagents coming from reservoirs 9 by introducing the needles of syringes 7 into said recesses by lowering said syringes. In the same way, it is possible to introduce into the recesses 13 doses of liquids coming from reservoirs 26 located in zone 8.

The reservoirs 26 contain samples of blood coming from donors. They are introduced into the device 1 via a conveyor means 30 which takes them successively to different treatment stations 31, 32 and 33, before taking them to station 34 where the syringes 7 of the arm 5 may take the liquid that they contain.

In this way, each recess 13 of the disc 12 may serve as recipient for reaction between a liquid coming from a reservoir 26 and a reagent coming from a reservoir 9.

To this end, the oscillating arm 5 must be able to rotate about its vertical axis, be lowered and raised along said vertical axis and must control the actuation of the syringes 7. FIGS. 5 and 6 illutrate an embodiment according to the invention enabling these results to be obtained.

As may be seen, the oscillating arm 5 is supported by the slave jack $VE_l$, disposed vertically so that its cylinder $h_l$ may rotate about the vertical axis 6 thanks to a bearing system 14 enabling it to move in rotation with respect to the frame 15 of the apparatus 1.

The oscillating arm 5 is borne by the rod $k_l$ of the piston of said slave jack $VE_l$. Furthermore, a rib and groove system 16 prevents the rod $k_l$ from rotating with respect to cylinder $h_l$.

In this way, thanks to the slave jack $VE_l$, the arm 5 may be raised and lowered parallel to the vertical axis 6.

Moreover, a tie 17 makes a loop 53 about the cylinder $h_l$ of the slave jack $VE_1$ and is connected, at one of its ends, to the piston rod $k_2$ of the slave jack $VE_2$ (possibly via a guide pulley 54) and, at its other end, to said frame 15, via a draw spring 55. The cylinder $h_2$ of the jack $VE_2$ is connected to the frame 15 (cf. FIG. 6).

In this way, thanks to the slave jack $VE_2$ and to the tie 17, the arm 5 may rotate about the vertical axis 6, the loop 53 rolling with friction on the cylinder $h_l$ of the jack $VE_1$ under the combined action of the jack $VE_2$ and of the spring 55.

In addition, as shown in FIG. 5, the arm 5 comprises a part 5a, fast with the rod $k_l$ of the slave jack $VE_1$ and bearing the bodies 7a of the syringes 7, and a mobile part 5b adapted to slide vertically with respect to the fixed part 5a, thanks to slide guides 56 and fast with rods 7b of the pistons of said syringes 7. The slave jack $VE_3$ is carried by the fixed part 5a, whilst the mobile part 5b is connected to the rod $k_3$ of said slave jack $VE_3$.

In this way, thanks to the slave jack $VE_3$, the syringes 7 may be actuated to take and deliver doses of liquid.

To examine the result of the agglutination which may result from the reactions in the recesses 13, the device 1 comprises a bar 35 of CCD diodes, disposed under the disc 12 opposite an illuminating device 36. The bar 35 and the illuminating device 36 are opposite the arm 5 with respect to the axis 11 and the bar 35 is at right angles to the vertical plane defined by axes 6 and 11.

The bar 35 examines by transparency the bottom 25 of each recess 13 in m observations each offset by one step. For all the recesses 13 of a radius 19 of the disc 12 to be examined each in m steps, the pin 11 of said disc is rendered mobile in horizontal translation, at right angles to said bar 35.

To this end, FIGS. 7 and 8 show that the pin 11 of disc 12 is fast with a carriage 37 mobile with respect to the base plate 38 of the device, fast with frame 15. This carriage 37 comprises a frame 39 bearing a motor 40 and a smooth bearing 41 for pin 11. The driven shaft of the motor 40 rotates a pulley 42 which is connected to a pulley 43 fixed on pin 11, via a notched belt 44. The carriage 37 is guided in translation by a rail 45 and it moves under the action of the slave jack $VE_4$, whose piston rod $k_4$ is connected to the carriage 37 by a rod 48, whilst the cylinder $h_4$ of said jack is fast with the plate 38.

In this way, the pin 11 may slide in a slot 49 in the base plate 38, parallel to the rail 45 and at right angles to the bar 35 of CCD diodes.

The carriage 37 may further comprise a vibrator 49 intended to animate the pin 11 in a reciprocating movement parallel to its axis, episodically against the action of a spring 50, in order possibly to shake the liquid contained in the recesses 13 in the disc 12.

In this way, when recesses $13_l$ to $13_p$ of the radius 19 lying in the plane defined by axes 6 and 11 must be read by arrangement 35 to detect and quantify the agglutinations (cf. FIG. 9), the disc 12 is advanced by the jack $VE_4$ in the direction of arrow $F_l$ so that the arrangement 35 is plumb with the outer limit 51 of the field 25 of the bottom of the first recess $13_l$. Then, step by step, the jack $VE_4$ is actuated m times for the n photosensitive elements of the arrangement 35 to examine said field 25 at n×m points. When reading of the field 25 of the recess $13_l$ is completed, the jack $VE_4$ moves the pin 11, still in direction $F_l$, so that the outer limit 52 of the field 25 of the bottom of the second recess $13_2$ arrives plumb with the photosensitive elements of the arrangement 35. This second recess $13_2$ is read in identical manner and the process continues until reading of recess $13_p$ has been completed.

The jack $VE_4$ then returns the pin 11 into its initial position (arrows $F_2$).

It is thus seen that the analyzing device 1 of FIG. 2 may operate with the aid of four slave jacks $VE_1$ to $VE_4$ of the device of FIG. 1. Of course, jacks $VE_1$ to $VE_4$ may be borne by mobile parts, the rest of the device, namely motor M, system a to d, master jack MV, control device DC, electro-valves $i_l$ to $i_4$, and reservoirs R1 and R2 being able to be fixed on the frame 15. The jacks $VE_1$ to $VE_4$ are connected to the electro-valves $i_l$ to $i_4$ by supple ducts.

What is claimed is:

1. A device for actuating an automatic device comprising a plurality of combined mobile members, comprising:
   (a) a single electric motor capable of rotating in both directions of rotation;
   (b) mechanical means for converting the movement of rotation of said electric motor into a movement of translation;
   (c) a hydraulic master jack whose piston is controlled in translation by said movement converting means;
   (d) a plurality of hydraulic ducts connected in parallel to the cylinder of said master jack;
   (e) a plurality of electro-valves each mounted on one of said hydraulic ducts;
   (f) a device for controlling said electro-valves;
   (g) a plurality of hydraulic slave jacks whose cylinders are each connected to one of said hydraulic ducts and whose pistons are each connected to one of said mobile members; and
   (h) a source of pressurized fluid permanently connected via a plurality of lines to the cylinders of the slave jacks, on the piston side thereof opposite the connecting ducts of the master jack.

2. The actuating device of claim 1 wherein the electric motor, the movement converting means, the hydraulic master jack, the elctro-valves and the control device are mounted in fixed manner.

3. The actuating device of claim 1 wherein each slave jack is connected to a source of fluid under atmospheric pressure, on the side of the intake of the fluid coming from the master jack, the connection between said source and said slave jacks being controlled by electro-valves under the dependence of the control device.

4. An automatic device which is actuated by the actuating device of claim 1.

5. The automatic device of claim 4, wherein the automatic device is for detecting and quantifying, in recipients of which at least the bottoms are transparent, agglutinates likely to be formed under the action of at least one liquid reagent, by particles in suspension in doses of liquids to be tested contained in said recipients, said automatic device comprising a linear arrangement of a plurality of photosensitive elements observing by transparency the bottoms of said recipients containing the possible agglutinates by scanning said bottoms of said recipients, so as to form n×m points of observation distributed over a rectangular or square surface occupying the major part of the surface of the bottom of each recipient, said recipients being constituted by recesses distributed along radii of a horizontal transparent disc adapted to rotate about its vertical axis and said automatic device comprising an oscillating arm rotating about a vertical axis along which it may slide and provided with means for taking and restoring liquid doses, and provided for taking such doses from reservoirs of reagents and liquids to be tested and for conducting them into said recesses in the transparent disc, whilst said linear arrangement of photosensitive elements is disposed horizontally in fixed manner at right angles to a diameter of the disc and the axis of rotation of the disc is mounted to move in translation at right angles to said arrangement of photosensitive elements, wherein the slide of said oscillating arm along the vertical axis, the rotation of said arm about said axis, the actuation of the means for taking and restoring the liquid doses and the translation of the axis of rotation of the disc are effected by four slave jacks.

* * * * *